United States Patent
Mansfield et al.

(10) Patent No.: US 6,283,914 B1
(45) Date of Patent: *Sep. 4, 2001

(54) DEVICE AND METHOD FOR MONITORING DIETARY INTAKE OF CALORIES AND NUTRIENTS

(75) Inventors: Elizabeth A. Mansfield, Silver Springs, MD (US); Jean-Pierre A. Kocher, Heidwiller (FR)

(73) Assignee: Jean-Pierre Kocher, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/170,098

(22) Filed: Oct. 13, 1998

Related U.S. Application Data

(63) Continuation of application No. 08/698,047, filed on Aug. 15, 1996, now Pat. No. 5,819,735.

(51) Int. Cl.[7] ........................................................ A61B 5/00
(52) U.S. Cl. ........................ 600/300; 705/3; 600/501; 128/920
(58) Field of Search ................................... 600/300–301; 128/897–898, 920–921, 903–904; 434/127; 235/375; 705/2–3

(56) References Cited

U.S. PATENT DOCUMENTS

| | | | |
|---|---|---|---|
| 5,233,520 | * 8/1993 | Kretsch et al. | 128/921 |
| 5,412,560 | * 5/1995 | Dennision | 128/921 |
| 5,796,640 | * 8/1998 | Sugarman et al. | 128/921 |
| 5,819,735 | * 10/1998 | Mansfield et al. | 600/300 |
| 5,836,312 | * 11/1998 | Moore | 128/898 |

* cited by examiner

*Primary Examiner*—Eric F. Winakur
*Assistant Examiner*—Michael Astorino
(74) *Attorney, Agent, or Firm*—Ronald P. Kananen; Rader, Fishman & Grauer

(57) ABSTRACT

A portable, autonomous electronic device consisting of a barcode scanner, an updatable nutrition facts database, user memory to store product records of products eaten, and an integral readout display is disclosed that will allow a user to scan barcodes on food items consumed and keep a cumulative total of calories and other nutrients. Prepared packaged foods may have their barcodes read directly, while foods that are used in cooking or preparing other foods may be referenced by scanning from a printed generic foods barcode list provided with the device. Serving sizes can be adjusted to accurately reflect the intake of given food items. Daily cumulative totals of calories and several other nutrients can be displayed as bar graphs, and the incremental increase that would result from consuring a scanned item can be displayed with reference to what has already been consumed. Weekly calorie totals broken down by day can be displayed in order to give an estimation of how successfully the user has adhered to diet goals over a dietarily significant span of time. Barcode numbers of food items input into the device along with date and serving size consumed can be stored in user memory and downloaded to another device, for example a computer or printer, via an interface. Diet strategies can be personalized with respect to any one of or combination of several nutritional categories, such as calories, fat, etc.

24 Claims, 7 Drawing Sheets

DEVICE AND METHOD FOR MONITORING DIETARY INTAKE OF CALORIES AND NUTRIENTS

This application is a continuation of 08/698,047 filed Aug. 15, 1996 now U.S. Pat. No. 5,819,735.

BACKGROUND—FIELD OF INVENTION

This invention relates to a device and method for diet control; more specifically, to an autonomous portable electronic device and method that can scan barcodes and relate barcode data to a nutrition facts database. This device can extract, display, and store in a cumulative fashion the nutrition data of scanned items and will allow the user to easily determine when calorie and nutrient limits have been reached in relation to a selected diet plan.

BACKGROUND—DESCRIPTION OF PRIOR ART

Controlling one's nutrition intake is a major focus of health maintenance. Moderation of caloric and fat intake is a common concern for the public, while precise control of sodium, protein and fiber, for example, are required for segments of the population whose health has been compromised by medically important conditions.

For many years, publications listing approximate calorie/fat/sodium, etc. content of generic, and sometimes brand-name items have been commonplace on supermarket checkout stands. These were used to monitor diet and required the user to look up the food item in question, estimate serving size and write down the nutritional values found for food items. This is time-consuming, tedious and gives only a coarse estimation of diet, and also requires a high compliance level by the dieter. More recently, the FDA began requiring labeling of food products with specific nutrition facts. This allowed the consumer to gain a more precise estimation of nutrition intake by using nutrition values determined specifically for the products in question. This is a clear advantage for diet monitoring, however, the time and effort required for recording the data remain as burdensome as before.

Several solutions have been proposed that seek to overcome the difficulty of looking up foods and making lists of what and how much was eaten. One early device (U.S. Pat. No. 4,321,674 to Krames, 1982) uses keypad entry of food types coupled to a user-defined daily calorie limit. This allows the user to enter the type of food eaten, how many servings eaten, and the device compares cumulative calorie consumption for the day to the user-set value. The user will be warned if the limit has been surpassed. This device, as a nutrition monitor, suffers from over-generalization about food types, as it only allows entry of categories of food such as milk, meat, vegetables or fruit products. This method of monitoring can give an approximation of calories or other nutrients consumed but is by no means precise. Additionally, it relies on the user to decide what the make-up of the food eaten is.

U.S. Pat. No. 4,686,624 to Blum (1987) improves upon this idea by adding a database that contains food names, such as semi-skimmed milk, rather than food categories. This allows a more precise calculation to be made of nutritional value of food consumed. However, this device calls for food items to be entered by using a cipher or mnemonic code that must be looked up for each food. Sakai, in U.S. Pat. No. 4,855,945 (1989) describes a similar device, but in which a nutrition facts database can be accessed by entering actual food names via an alphanumeric keypad. While these methods of entry are a vast improvement in specificity for particular food item nutrition data, they still present several challenges for the user, as do all the previous efforts described herein. Most notably, entry by typing on a keypad is non-ideal for several reasons. First, and most importantly, it is a slow inefficient way to enter data. Second, one can easily imagine a user who is not proficient in the language in which the database is stored, will have difficulty in correctly entering food names, codes or the like, in a language with which he is not familiar. Third, manual entry by typing of food names is an obstacle to use of the device by those with minimal language skills in any language, and to those who have difficulties with dexterity.

Another limitation of the aforementioned patents is that their food databases are keyed to food names or categories. The prevalence of specific brand formulations and the differences between these formulations with respect to nutrition are becoming increasingly important in today's marketplace. One can have only limited expectations that different brands of a particular food type will be similar in nutrition value, therefore, narrowing nutrition data to generic descriptions of food items will in all probability be misleading for the dieter and result in erroneous assumptions about one's nutritional intake.

The problem of strictly generic databases has been addressed in U.S. Pat. No. 4,891,756 to Williams (1990), wherein the device and method of operation are fundamentally the same as that of Sakai, but a brand-specific database has been provided rather than a purely generic food item list. This idea is important, changing the nature of the device to one in which the user no longer has to guess what the components of foods are, rather a specific branded food such as Kellogg's Corn Flakes can be entered. However, the database of this patent is arranged in a hierarchical manner, where the user is required to sift through multiple levels of food groups to finally arrive at the food item desired to be entered. This is clearly tedious and time-consuming. Also, the disadvantage of using manually typed entry still limits the usefulness of this device. Finally, the nutritional database that is proposed is not updatable, so that no new information can be entered into the device. This of course precludes being able to identify new products that are introduced in the market after the device has been programmed.

The prior devices are therefore firstly limited by the requirement for item identification entry through a keyboard which means that some ability to make food identification and to type is involved. Generally, none of these devices can be described as simple to use, based on the amount of decision-making and/or keystroke entry that is required to use them. They are secondly limited by databases that cannot be updated.

A more simple and novel method of identifying food items is through the unique identifier provided by product label barcodes, such as are commonly used in commercially prepared foods. Barcode scanning is quick and basically demands no decision making by the user. Product barcode scanning rather than keypad entry for food identification has been introduced. U.S. Pat. No. 5,478,989 (1995) to Shepley discloses a device that compares nutrition information about specific products with personal health data of the user. A nutritional database in which products are related to their corresponding nutrition facts by barcode is proposed as the source for nutrition information. This device aids consumers in making informed food choices with respect to nutritional value and predicts desirability of individual food items based on personal information input into the device by the user. This system is directed to making favorable food choices but is primarily predictive meaning that it may be used to make decisions about which foods to buy or consume. What is not provided is a retrospective cumulative survey of what and how much was actually consumed, in other words, the device is not a monitor of eating activity, but rather an aid to choosing nutritionally correct foods.

U.S. Pat. No. 5,412,564 to Ecer (1995) discloses a device that allows users to obtain nutrition information about the products they buy in grocery stores and restaurants, which may be entered by scanning barcodes and which information is stored on a smart card. General breakdowns of nutrition are made by averaging all purchased items and dividing the values obtained by numbers of days and numbers of household members over which the food is distributed. Thus, for example, a family could determine that its average "fat calories as % of total calories" was 30%. This information, while informative in a general sense, is not specific for a single person unless that person is the unique user of the system, because information for an individual is provided as a fraction of the total, not as what the individual actually consumed. Additionally, this device relies on data collected from what is purchased rather than what is actually consumed and thus cannot give daily breakdowns of nutrition consumption, as might be required for a user wishing to use the system for daily medical diet control.

Another problem that is common to the two previous devices is that they are not autonomous, in the sense that they are both dependent for function on additional hardware that is not in the possession or control of the user. Therefore, the user is constrained to patronize establishments that have chosen to provide the necessary complementary hardware.

It can be seen from the information presented above that no device yet proposed takes advantage of the power of a barcode scanner for daily precise monitoring of nutrition consumption using an updatable brand-specific nutrition facts database.

It would be advantageous for an individual to be able to track actual consumption of dietary components using a simple method and with an easily portable versatile device. Optimally, the device would require minimal manipulation and decision-making by the user.

OBJECTS AND ADVANTAGES

Accordingly, several objects and advantages of our invention follow. In the ensuing description of objects and advantages, and through the rest of the specification, "product record" may be understood to mean barcode-related nutrition data, as stored in nutrition facts databases, such as nutrition facts and serving size, and may also include additional information such as company-related information, savings coupons, or advertisements for a specific product.

Some primary objects of the invention are:
(a) to provide a diet monitoring device that is portable, and of a size and construction that will allow it to be conveniently carried anywhere, for example in a handbag or briefcase. Easy portability will encourage use by the dieter.
(b) to provide a device that is autonomous in the sense that it doesn't require for its function any additional hardware that is not in possession or under the control of the user.
(c) to utilize a barcode scanner as the input mechanism for recording the items eaten, so that the user is not required to make any decisions about the category or composition of food that is being entered. Because the barcode identifies a unique product, the device can automatically specify food brands, which can be expected to have unique compositions, as opposed to using food names, which are usually general; for example, corn flakes made by different manufacturers may have different nutritional values. Moreover, any kind of information about a product, in addition to nutrition facts data, can be sorted and retrieved by barcode number. This gives the possibility of presenting data related to a product, for example company telephone numbers or advertisements, when the product barcode is scanned.
(d) to track personalized nutritional goals for individual users using nutrition data that is as precise as possible and serving-size-adjusted for the foods eaten. In many instances, the user will decide to consume more or less than a predetermined serving size of a product. When this occurs, in order to have a very accurate diet estimation, it is necessary that the actual amount consumed be recorded.
(e) to provide a program that automatically performs predetermined calculations on nutrition data retrieved from product records, without user intervention. This will limit manipulation mistakes and improve the user-friendliness of the device.
(f) to allow for the design of a personal diet strategy based on limiting the consumption of one or more nutrient types, such as calories or fat, so that the user can choose which aspects of diet he would like to control.
(g) to display a simple graphical record of nutrition consumption that shows both how much of a chosen total has been consumed and how much is still available within the diet limit strategy. Graphic representation of data provides a rapid and easy way to evaluate the state of the diet.
(h) to include two kinds of databases: a general nutrition facts database (GNFD), which is a more global database including product records of a large number of foods, and a personalized nutrition facts database (PNFD) which is dynamically built by transferring the food records from the GNHD of products purchased and/or eaten by the user. Because the number of products in the general nutrition facts database will be very large, the time required for a database search will also be relatively large. Therefore, it is desirable to create a smaller user-specific subset database that contains the product records of only the items that a user has purchased or consumed. After a period of time, this subset database will largely be able to substitute for the GNFD. At any time, however, when a product is not found in the PNFD, the GNFD will be subsequently searched.
(i) to allow the automatic building of the subset database (PNFD). When product barcodes are scanned to be entered for diet monitoring purposes, a search is made for the product record in the PNFD. If the product record is not found in PNFD, the search is continued in GNFD, and if the product record is found there, an automatic transfer of the product record is made from the GNFD to the PNFD. This process will build a database of products the user has consumed. If the same product is consumed on a later occasion, its product record will be found directly in the PNFD without the need to search the GNFD. If the product whose barcode was scanned is found in neither database, the user is alerted.

(j) to allow transfer of product records from the GNFD to the PNFD by scanning product barcodes, without influencing the diet survey. This will allow the user to update the PNDF with product records of foods he has purchased but has not yet eaten. As an example, if the GNFD is provided by stores and includes the records of the products they sell, this option will allow the user to update the PNFD by scanning the products he selects while shopping in different stores. Later, when the purchased products are to be consumed, the GNFD will not need to be searched, because the product records will already be stored in the PNFD. This will eliminate the need to perform searches in multiple GNFDs to find particular products from different stores when purchased products are consumed.

(k) to provide updatable nutrition facts databases. Databases will be contained either in a non-removable memory fixed in the device, or will be in a removable plug-in type of memory such as an PCMCIA SRAM or Flash Memory Cards. If the databases are contained in non-removable memory, they can be updated by interface with an external device. If the database is stored in removable memory, it can be updated by replacing the obsolete database with a new version. Using removable memory, which can easily be exchanged on the device, presents a further advantage, which is that if the database is very large, it can be split into categories, such as brands sold in particular regions of the country, or brands carried by particular supermarket chains, and stored on more than one memory card.

(l) to accumulate in integral or removable user memory the nutrition information, serving size, date and time of consumption for food items that are entered into the device over a dietarily significant span of time. This will make it possible to keep track of the food brands and amounts consumed during this period of time. This data can be analyzed by a specialist to aid the user in controlling his diet.

(m) to allow downloading of accumulated product records to other devices by memory card transfer or interface, for analysis of long-term dietary habits. This allows the examination by a second party of specific consumption information in several nutritional categories that would otherwise be burdensome for the user to record manually.

Additionally the device incorporates a number of other features which when combined serve to provide a simple and powerful way to monitor diet.

Further objects and advantages of our invention will become apparent from a consideration of the drawings and ensuing description.

DRAWING FIGURES

Figure 1:
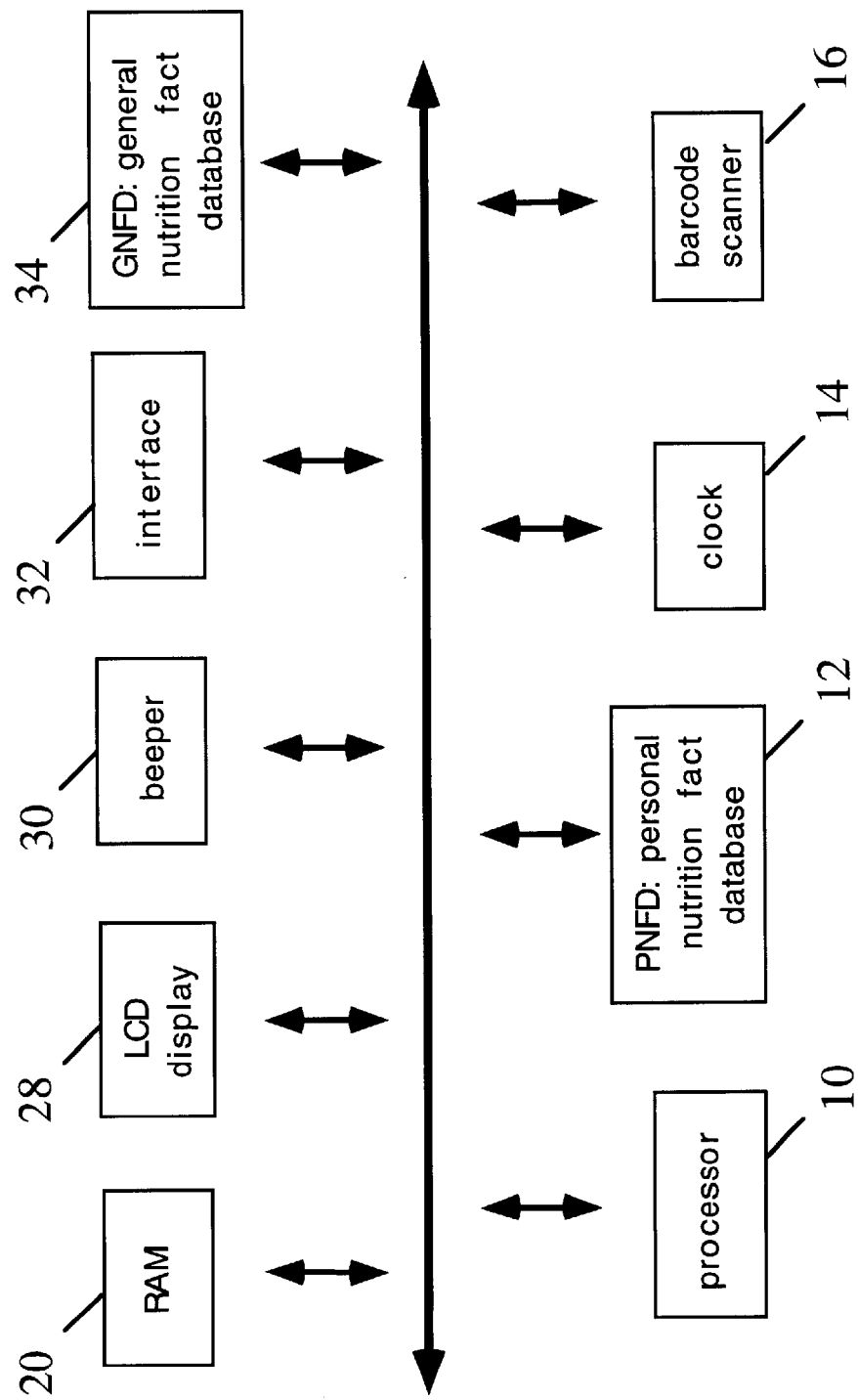
FIG. 1 is a block diagram of the product identification, recording and monitoring components in accordance with the preferred embodiment of the invention, in which there are two database memories, the first storing a general nutrition facts database and the second storing a personalized nutrition facts database.

| Reference Numerals in Drawings | |
|---|---|
| 10 processor | 12 PNFD memory |
| 14 24-hour clock | 16 barcode scanner |
| 18 scanner on-switch | 20 user memory |
| 22 6-way switch | 24 set wheel |
| 26 validation switch | 28 LCD display |
| 30 beeper | 32 interface |
| 34 GNFD memory | |

DESCRIPTION OF THE PREFERRED EMBODIMENTS—FIG 1

The description that follows relates to a general identification of the invention. Specific identification of microchips, barcode scanners and other elements used in the manufacture of the device, or the manner of interconnecting the elements, are not shown in detail in the drawings or described in the specification. One reason for this is that technological advances are very rapid and materials that can be obtained and used at the outset of development may be expected to be readily superseded by newer and more advanced technology. A second reason is that at any given time, a person skilled in electronics or computer design can select the most appropriate components and methods for connecting them, to construct the device described after careful study of the description that follows.

In the preferred embodiment and according to FIG. 1, the system consists of means such as a processor 10 under the control of a prestored program, incorporating means for entering product identification, such as a barcode reader or scanner 16. A scanner on-switch 18 activates a barcode scanner 16. Barcodes are related to their respective product records which are stored in nutrition facts databases on two removable memory modules. A GNFD memory 34 contains a general nutrition facts database (GNFD) comprising a brand-specific nutrition facts database with barcode numbers and product nutrition facts data. A PNFD memory 12, stores a personalized nutrition facts database (PNFD) that is built using product records from GNFD.

Processor 10 is connected in a known manner to means such as a user memory 20 where product records of all products consumed over a period of time are kept. These product records will include serving size and nutrition values related to product barcodes that are input into the device. The product records will be tagged with a time/date of consumption that is provided by means such as a 24-hour clock 14. User memory 20 also contains diet default values for specific nutrition categories that are relevant to health maintenance, including calories, sodium, fat, saturated fat, cholesterol, carbohydrates and fiber, which are based on currently available health maintenance advisories. The user may be alerted to excessive consumption over the selected limit in a nutrition category by means such as an audible beeper 30 that sounds when preset limits have been exceeded. An interface 32, such as a serial or parallel port or infrared transmitter, is used to exchange data between this device and an external device, for the purpose of updating a database or for data analysis at a remote location.

As shown in FIG. 1, the main embodiment of the device also incorporates means such as a 6-way switch 22 for changing the mode that the user wishes to set, with choices including input/display of data derived from scanned items, transfer of nutrition facts data from the general database to the personalized database, setting of diet parameters, correcting input, setting time, and interfacing with an external device. In order to change parameters such as serving size and diet category limits, means such as a set wheel 24 is provided. A validation switch 26 is provided for validating any operation or setting. Display means such as an LCD display 28 shows product and nutrition information and any other alphanumerical information, in addition to bar graphs or other ways of displaying daily and weekly accumulated nutrition information.

Several alternate embodiments are envisioned concerning the configuration of the database memories. In the first, PNFD memory 12 is located internally and the GNFD is located on removable, updatable GNFD memory 34. Barcode and nutrition facts of scanned items are copied from removable GNFD memory 34 into internal PNFD memory 12, which is an integral part of the device and cannot be removed.

In a simpler embodiment, both PNFD memory 12 and GNFD memory 34 are located in internal, non-removable memory. In this embodiment, the GNFD provided with the device is updatable by connection of the device through interface 32 to an external device which downloads new nutrition facts data to the GNFD memory 34. As new products are scanned, the PNFD is updated automatically from the GNFD and PNFD memory 12 is used as the primary search database when products are entered for diet monitoring.

Operation—FIGS. 3A–E

Figure 2:
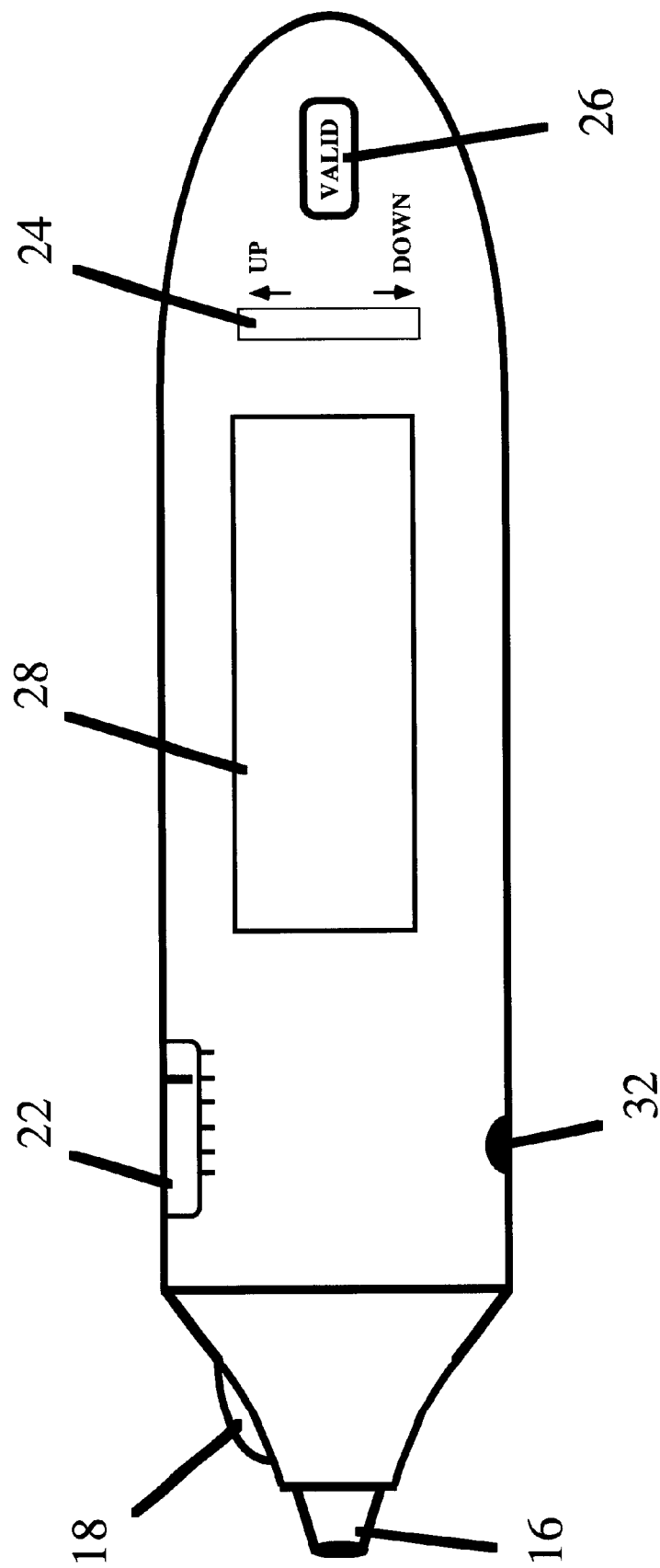
FIG. 2 shows an example of the preferred device assembly.

This invention specifies an electronic device that is sufficiently portable to be carried and used anywhere. The most preferred embodiment incorporates a processor 10, an integral barcode scanner 16, a clock 14, a display 28, preferably of the LCD type, a user memory 20, and two removable memories 12 and 34 containing nutrition facts databases, PNFD and GNFD, respectively. The device is preferably encased in hard plastic with or without a rubberized coating to protect it from impact damage, and can be held in the hand in a manner similar to a writing pen. FIG. 2 represents one construction of the invention, but other constructions and configurations are possible.

The method of operation described herein is given merely as an example of how the device could be constructed and used, but is not meant to limit the scope of either the hardware or the software components of the invention, nor to limit the method of operation to the steps described here.

Six modes can be selected on the device using 6-way switch 22: time/date mode to set the time and date parameters; diet set mode to enter daily diet limit values for calories and other nutrients specific to a diet strategy; input/display mode, in which the input mode is used to add new food items to the nutrient survey, and the display mode gives a display of the daily nutrient intake and the weekly calorie summary; correction mode to correct data input by error or which later needs to be deleted; a PNFD-transfer mode which is used to transfer product records from the GNFD to the PNFD; and an interface mode, which is used to transfer data to or from an external device.

Figure 3A:
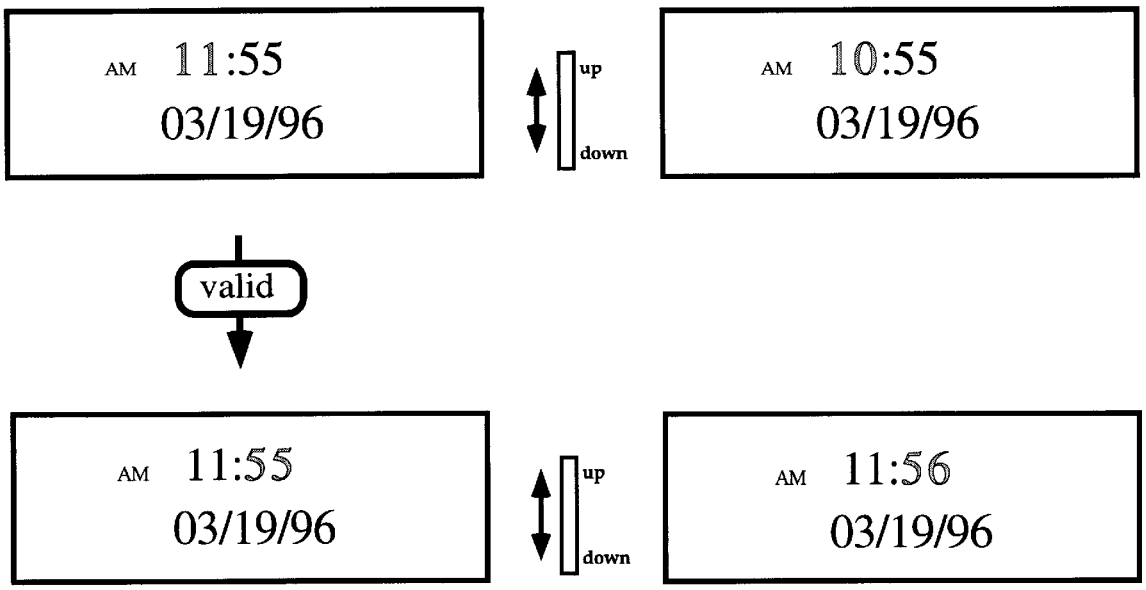
FIG. 3A shows the operation of setting the time and date

Mode I: Time/date setting (FIG. 3A)

The device includes a clock 14. Time and date records will be attached to each item input into user memory 20, therefore it is important to have the time/date functions set to the appropriate values. Nutrition data of scanned items is accumulated in 24 hour periods. To set the time and date, 6-way switch 22 must be set on "time/date set". When this mode is selected, the "hour" portion of the clock will begin to blink. Set wheel 24 is turned to change the numerical value of the blinking portion. When the correct number has been chosen, validation switch 26 is depressed and the next value, "minutes", is displayed. Each value (hours, minutes, day, date and year) is set as described above, depressing validation switch 26 when the correct numerical value has been chosen. When the settings are correct, 6-way switch 22 is returned to "input/disp" mode.

Figure 3B:
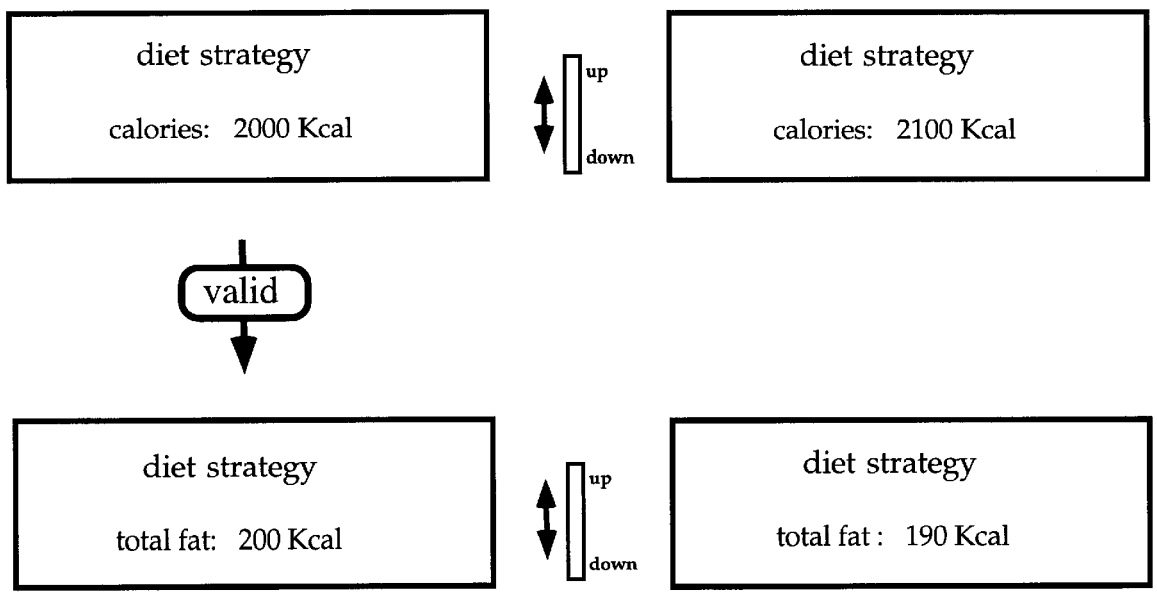
FIG. 3B shows the operation of setting the diet limits

Mode II: Diet strategy setting (FIG. 3B)

In the preferred embodiment, the device includes preset default dietary limits for calories, fat, saturated fat, cholesterol, sodium, dietary fiber and total carbohydrate based on USDA recommended levels. These values, and any other displayed data are calculated and displayed in a completely hardware-independent manner, therefore the device can display any number of values, and will not be limited by the description given here. With reference to diet limit values, because people will frequently want to tailor diets to their specific needs, dietary limits in the device can be changed to different values. To select a diet program, meaning to set numerical limits on the amount of one or more nutrition values, 6-way switch 22 is moved to the "diet set" position. Any diet parameter can be selected to be set as a limit and any numerical limit can be set. When 6-way switch 22 is placed in the diet set position, the first display on display 28 will appear showing the word "calories" and a default value of 2000. The nutrient parameter to be set can be changed by pressing validation switch 26 until the parameter desired to be set, for example calories, appears. Pressing validation switch 26 enters the numerical value shown for the nutrient parameter that appears on display 28. The numerical default value for each nutrient can be changed by selecting that nutrient with validation switch 26 and turning set wheel 24 up or down to raise or lower the value of the displayed numeral. When validation switch 26 is pressed, the value shown on the display will be entered and will remain at the set value until it is changed again.

Figure 3C:
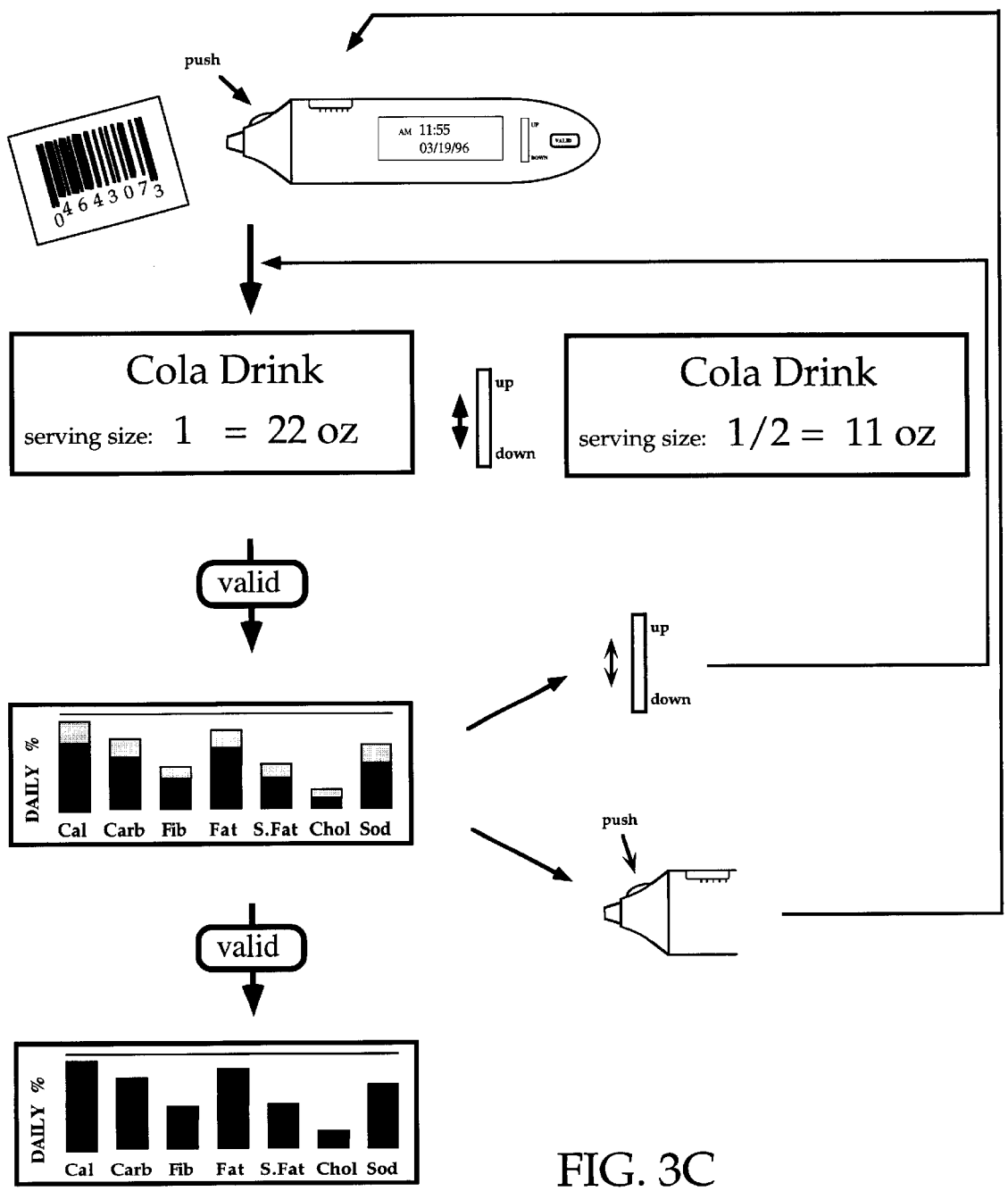
FIG. 3C shows the operation of inputting product barcode identification

Mode IIIa: Input (FIG. 3C)

To scan a new product barcode, 6-way switch 22 is placed in the "input/disp" position. The time and date are displayed when 6-way switch 22 is on "input/disp" or when the device is in standby mode. The device returns to and remains in standby mode whenever there is no activation of any operation for a given amount of time, for example 5 minutes. In "input/disp" mode, the time and date will be displayed until scanner on-switch 18 is depressed. Integral barcode scanner 16, preferably of the wand type, but otherwise of the laser or CCD or other type, is used to enter food item barcode identification into the device by depressing and holding down scanner on-switch 18 and passing scanner 16 over the barcode printed on products. Some foods, for example certain fresh vegetables, will not have nutrition facts labels. These generic foods will have arbitrarily assigned barcodes that can be scanned from a booklet provided with the device. Using the scanned barcode number, processor 10 performs an automatic search first in the PNFD, and if the product is not found, in the GNPD, to retrieve the nutrition information pertaining specifically to the product scanned. When a barcode has been correctly read, but the food item is found neither in the GNFD nor in the PNDF the device activates beeper 30, emits a unique warning beep and goes back to standby mode. If the product record related to the scanned barcode is found, the device will activate beeper 30 and emit a unique beep. In input/display mode only, if the product record of the item was only found in the GNFD, a copy of this product record is automatically transferred into the PNDF. Following this operation, the name of the product as well as the serving size that is given on the nutrition facts label will be shown on display 28.

At this time, if the actual amount of the product consumed is less or more than the suggested serving size, serving size consumed can be adjusted to fractional or multiple values of the given serving size using parameter set wheel 24. When the correct serving size value is displayed, validation switch 26 is depressed to enter the serving size choice.

After setting the serving size, the percentage of each of the relevant nutrients in the scanned product is automatically computed and displayed on display 28 in bargraph format with two regions of different color, such as black and gray. The black region of each bar represents the total amount of calories and nutrients already consumed. This amount is displayed as a percentage of the threshold amount defined by the diet program. For example, if a calorie limit of 2000 calories has been chosen, and 1500 have already been entered on the device as consumed calories, a black bar will extend up to the 75% level in the calorie category. The gray region of the bar graph represents the increase in calories and nutrients that will result if the product that has just been scanned is consumed. If the increase represented by the gray region causes the total to exceed 100% of any nutrition value, the user will be warned by a unique beep that the selected diet limits will be surpassed.

If, upon scanning in a product barcode and viewing the increase in nutrient levels that would result from eating that product, the user finds that consuming the product is incompatible with his diet program, he has several additional choices. First, if he wants to consume the product but in a different serving size than the one shown on display 28, he can modify the serving size by moving set wheel 24 as described above. Turning set-wheel 24 causes the display to return to serving size setting. Second, if the user decides not to consume the scanned product but would like to try another product, he can scan a new product by activating scanner on-switch 18. Third, if he decides that no product will be consumed, he can push scanner on-switch 18 without reading any barcode. This operation will return the device to standby state (i.e. displaying time and date). Nothing will be stored in user memory until validation switch 26 is depressed a second time.

If the input product is compatible with user's diet strategy, and the product is eaten, the user confirms the choice by depressing validation switch 26. For each validated item, a product record will be made in user memory 20 of the barcode number of the product, the time/date of entry of the product and the serving size selected. When the item entered is validated, the gray regions of the bar graph described above will subsequently appear black, giving a running total for the days consumption. A product record is stored in user memory 20 for each item entered into the device which is validated and not deleted. Records can be accumulated for an extended period of time, which is defined by the amount of memory available. A recording period of at least two months would be most convenient for the user to be able to track eating patterns, but the actual period will be dependent on the size of the user memory provided with the device.

Figure 3D:
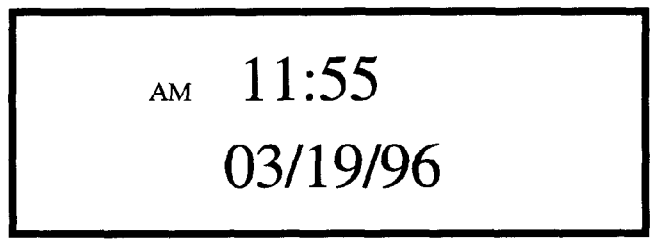
FIG. 3D shows the operation of displaying nutrition value graphs
Figure 3D:
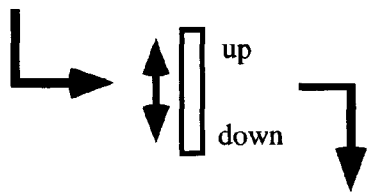
Figure 3D:
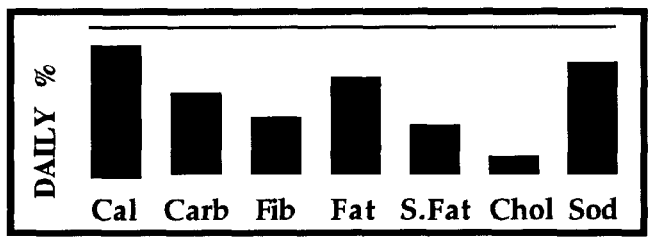
Figure 3D:
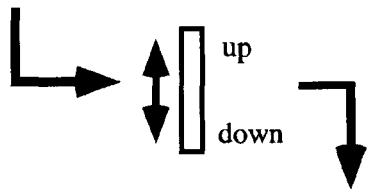
Figure 3D:
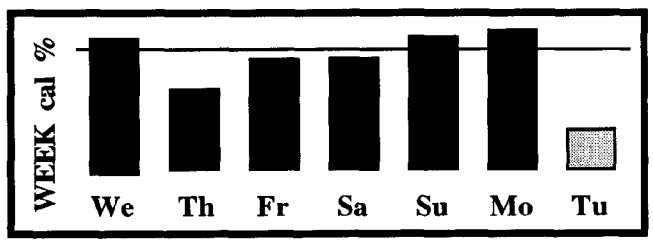

Mode IIIb: Display (FIG. 3D)

To view the daily nutrient accumulation bargraph or the weekly calorie consumption bargraph without entering a new product, 6-way switch 22 is placed in the input/display position. Turning set wheel 24 one stop displays the daily nutrient accumulation. In this mode, a bar graph representing the amount of calories and nutrients that have been consumed are displayed on display 28. The calories and nutrients consumed are shown as a percentage of the maximum value dictated by the selected diet program. For a given category (e.g. calories, fat), when the height of the bar reaches the top of display 28, 100% of the allowed amount has been consumed. Ideally, at the end of the day, meaning after the last food has been eaten, the percentage of calories, fat, saturated fat, cholesterol and sodium should be less than or equal to 100% of the amount defined in the diet strategy.

The daily summary is automatically reset to zero every 24 hours. However, because calories are often the most important criteria to be followed for the diet, the daily calorie consumption will be saved in a running seven-day record which can be displayed by the user. While in input/display mode, turning set wheel 24 two stops displays the weekly calorie consumption totals as a percentage of the diet limit value set by the user. In this mode, each bar on the graph represents one day. The amount of calories that have been consumed each day are represented by the height of the bar for that day. For weekly calorie display, values greater than 100% can be displayed and adherence to the selected diet strategy in terms of calories can be seen.

Figure 3E:
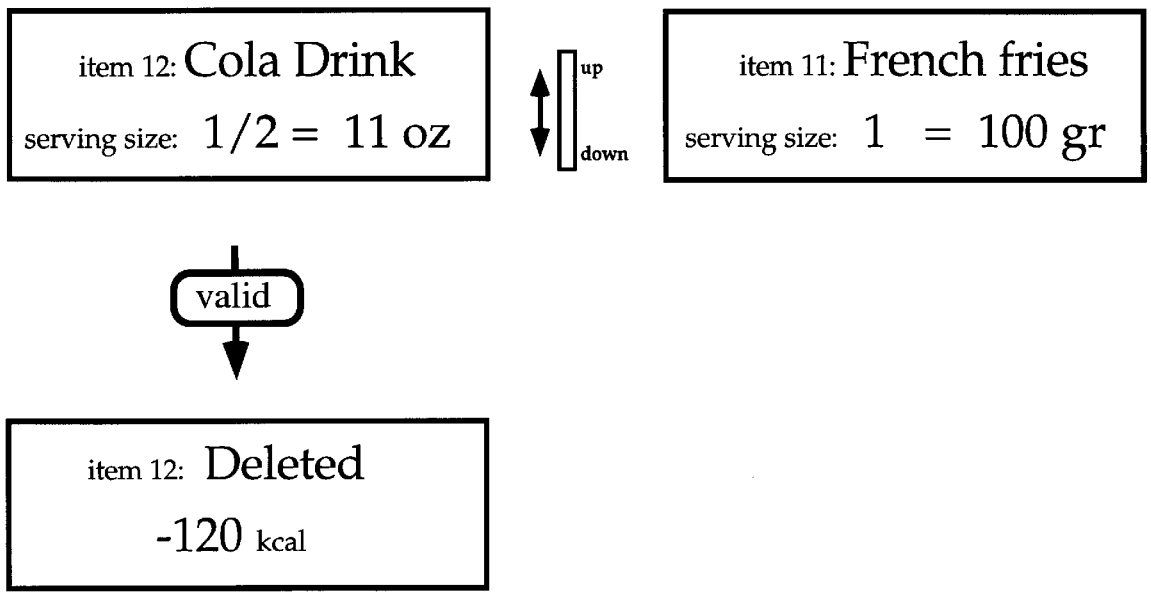
FIG. 3E shows the operation of correcting input data

Mode IV: Correction (FIG. 3E)

The barcode number, serving size and time/date of entry records for each product entered are saved in the memory of the device. However, once an item is entered and validated, it may subsequently be deleted by using the "correct" function. In correction mode, the product record of any previously entered product of the day can be deleted, however, once every twenty-four hours, the daily nutrition totals are finalized and product records can no longer be deleted. To delete an item within the 24-hour recording period, the 6-way set-switch is moved to the "correct" position. The name and serving size of the last item entered will be displayed on display 28. To delete the item on display 28, validation switch 26 is depressed and the words "deleted" and the numerical nutrient values deleted are shown. To select an item to delete that was entered previously to the last item, set wheel 24 is turned until the item desired to be deleted is located, then validation switch 26 is depressed as above.

Mode V: Transfer to PNFD

The personalized database (PNFD) can be created and updated by transferring records of barcode-scanned products from the GNFD without affecting the diet accounting. This subset of information is then available for more rapid searching when the user enters a barcode of a product to be consumed. To transfer information from the GNFD to the PNDF, 6-way switch 22 must be set on "PNFD transfer". A product is then entered by depressing scanner on-switch 18 and scanning the barcode of the item. The product record of this item is then added to the PNFD if there is no identical product record already stored there.

Mode VI: Interface

A serial or parallel port connection or infrared transmitter is provided for interchange of data between the device and an external device. To use the interface mode, 6-way switch 22 is set to "interface". This mode can be used to send and receive data between the device and an external computer. Data such as the user-defined parameters (diet strategy) and food product records can be downloaded from the device to the computer in order to be printed or for further analysis, such as for medical diet control. Data can also be sent from the computer to the device, providing an alternate way to update the nutrition fact database.

SUMMARY, RAMIFICATIONS, AND SCOPE

It can be understood from the previous description that the diet monitor and method of this invention can be used to easily and quickly assess the nutritional intake of an individual when used to scan barcodes and process nutritional data facts obtained thereby. The user can keep a running daily total of nutrition intake and view what portion of a selected diet limit has been consumed and what remains available within the limit set. This device and method permit control of diet factors such as calories and fat and the device accumulates product records of every food item entered. Depending on the configuration of the memories, accumulated nutrition information can be saved either in an internal memory or on a removable memory card. In either case, the cumulative record can be downloaded by exchanging the memory card onto another device or by connection of the device to an external device through a serial or parallel port or infrared transmitter. The cumulative data is then available for analysis by a health care professional, or anyone interested in the short, medium or long-term eating habits of the user. The ability to enter food item identification by scanning barcodes virtually eliminates guesswork on the part of the user as to the composition of the food item in question and minimizes errors in entering data. Additionally, control of the serving size actually consumed is provided, so that over- and under-estimation of recorded consumption are minimized. Portability of the device will allow its use almost anywhere, and encourage compliance by users. Updatable and dynamically built nutrition facts databases provide efficiency and flexibility to the device.

Although the description given above includes many specific examples of currently envisioned embodiments of the device, these possibilities should not be understood as limiting the scope of the invention but rather as providing illustrations of some of the embodiments that are now preferred. Several examples of alternate embodiments are also described.

Therefore, the claims that follow and their legal equivalents, rather than the examples given in the specification, should determine the scope of the invention.

We claim:

1. A portable consumable intake monitor comprising:
   (a) a barcode scanner for inputting product identification of a consumable intended to be consumed at the time of consumption;
   (b) a mode selector for selecting between a plurality of operating modes;
   (c) a parameter selector for selecting between a plurality of parameters associated with each of said plurality of operating modes;
   (d) a general database memory storing a database comprising a comprehensive set of barcode-sorted consumable product information including nutrition facts and other product-specific information;
   (e) a personal database memory storing a database comprising barcode-sorted consumable product information of items entered by a user;
   (f) a data transfer module for transferring said barcode-sorted product information from said general database to said personal database;
   (g) a user memory for storing user-input operational parameters;
   (h) a processor under the control of a prestored program for retrieving data from said databases, performing computations on retrieved data and administering adjustment and storage aspects of input data; and
   (i) a display for displaying product records and data derived from computations described in said program.

2. The portable monitor as in claim 1, wherein said memories are provided by removable read/writable memory cards.

3. The portable monitor as in claim 1, wherein said database memories are updatable by downloading data from an external device using a communication interface.

4. The portable monitor as in claim 2, wherein said databases can be updated by inserting new memory in which a new database is stored.

5. The portable monitor as in claim 1, wherein inputted products, their nutrition facts information and input time and date are accumulated in said user memory for long-term tracking of eating habits.

6. A method for monitoring dietary intake of nutrients over defined temporal periods, comprising steps of:
   (a) selecting a diet strategy based on cumulative daily totals of one or more nutrients;
   (b) entering product identification by scanning a product barcode;
   (c) selecting serving size to be consumed;
   (d) relating barcode identification to prestored nutrition facts database, said nutrition facts database including a global barcode-sorted nutrition facts database and a personal barcode-sorted nutrition facts database;
   (e) displaying the prospective increase of nutrients with comparison to the selected diet strategy limits;
   (f) validating said product and serving size choice and correcting undesired products or serving sizes;
   (g) performing computations on nutrient values of entered products and storing results of said computations in memory;
   (h) displaying results of computations.

7. The method as in claim 6, wherein barcodes are scanned from a printed publication listing a multiplicity of food items.

8. The portable monitor as in claim 1, wherein said plurality of operating modes consist of time/date setting mode, diet strategy setting mode, input mode, display mode, correction mode, data transfer mode, and interface mode.

9. The portable monitor as in claim 8, wherein said diet category strategy setting mode includes setting diet limits of calories, fat, carbohydrates, sodium, saturated fat, cholesterol, protein, and fiber.

10. The portable monitor as in claim 8, wherein mode selector is a six position switch wherein each position corresponds to each of said plurality of operating modes.

11. The portable monitor as in claim 1, wherein said parameter selector is a rotary input device.

12. The portable monitor as in claim 1, wherein said parameter selector is a switch.

13. The portable monitor as in claim 1, further comprising a palm-sized unitary housing containing all of the above mentioned components adapted to be transported and used in a hand of the user.

14. The portable monitor as in claim 1, further comprising a real time clock connected to said processor for maintaining date records and for delimiting 24 hour periods.

15. The portable monitor as in claim 1, further comprising a communication interface for exchanging information between said monitor and external devices.

16. The portable monitor as in claim 15, wherein said communication interface is a serial, parallel, or infrared communications interface.

17. The portable monitor as in claim 1, further comprising an alarm for alerting the user.

18. The portable monitor as in claim 17, wherein said alarm produces an auditory warning.

19. The portable monitor as in claim 1, wherein said barcode-sorted consumable product information includes brand-specific nutritional facts found on nutritional facts labels of commercial food products.

20. The portable monitor as in claim 1, wherein said product identification is a Universal Product Code (UPC) barcode.

21. The portable monitor as in claim 1, wherein said product identification is a barcode in a printed publication listing a multiplicity of food items.

22. The method as in claim 6, wherein said personal barcode-sorted nutrition facts database is automatically built from said global barcode-sorted nutrition facts database by scanning barcodes of purchased items and copying records of scanned items from global to personal barcode-sorted nutrition facts databases.

23. The method as in claim 6, wherein said nutrition facts database includes brand-specific nutritional facts found on nutritional facts labels of commercial food products.

24. The method as in claim 6, wherein said product identification is a Universal Product Code (UPC) barcode.

* * * * *